US006919312B2

(12) United States Patent
Mochizuki et al.

(10) Patent No.: US 6,919,312 B2
(45) Date of Patent: Jul. 19, 2005

(54) BONE-PATHOBOLISM TREATING AGENT

(75) Inventors: Shinichi Mochizuki, Minamikawachi-machi (JP); Nobuaki Fujise, Ishibashi-machi (JP); Chiharu Masuyama, Ishibashi-machi (JP); Eisuke Tsuda, Minamikawachi-machi (JP); Kanji Higashio, Kawagoe (JP)

(73) Assignee: Sankyo Co., Ltd., Tokyo (JP)

( * ) Notice: Subject to any disclaimer, the term of this patent is extended or adjusted under 35 U.S.C. 154(b) by 163 days.

(21) Appl. No.: 09/834,008

(22) Filed: Apr. 12, 2001

(65) Prior Publication Data

US 2001/0031725 A1 Oct. 18, 2001

Related U.S. Application Data

(63) Continuation of application No. PCT/JP99/05963, filed on Oct. 28, 1999.

(30) Foreign Application Priority Data

Oct. 28, 1998 (JP) ............................................ 10-322874

(51) Int. Cl.[7] .......................... A61K 38/00; A61K 49/00
(52) U.S. Cl. .............................. 514/12; 514/2; 424/9.1; 530/350; 536/23.1; 435/69.1
(58) Field of Search ................ 514/2, 12, 54, 514/56, 59; 530/350; 536/23.1; 435/69.1, 366; 424/9.2

(56) References Cited

U.S. PATENT DOCUMENTS

| | | | |
|---|---|---|---|
| 5,545,722 A | 8/1996 | Naka | 530/399 |
| 5,736,506 A | 4/1998 | Naka | 514/2 |
| 6,015,938 A | 1/2000 | Boyle et al. | |
| 6,214,838 B1 | 4/2001 | Sohda et al. | |
| 6,284,485 B1 | 9/2001 | Boyle et al. | |
| 6,284,728 B1 | 9/2001 | Boyle et al. | |
| 6,284,740 B1 | 9/2001 | Boyle et al. | |
| 6,288,032 B1 | 9/2001 | Boyle et al. | |
| 6,369,027 B1 | 4/2002 | Boyle et al. | |
| 6,613,544 B1 | 9/2003 | Boyle et al. | |
| 6,693,175 B2 | 2/2004 | Yano et al. | |
| 2002/0004207 A1 | 1/2002 | Yano et al. | |
| 2002/0051969 A1 | 5/2002 | Goto et al. | |
| 2003/0045456 A1 * | 3/2003 | Yamamoto et al. | 514/8 |
| 2003/0139325 A1 * | 7/2003 | Yamamoto et al. | 514/8 |
| 2003/0153048 A1 | 8/2003 | Goto et al. | |
| 2003/0181418 A1 | 9/2003 | Kumakura et al. | |
| 2003/0207827 A1 | 11/2003 | Boyle et al. | |
| 2003/0216297 A1 | 11/2003 | Kumakura et al. | |

FOREIGN PATENT DOCUMENTS

| | | | |
|---|---|---|---|
| EP | 0 784 093 A1 | 7/1997 | |
| EP | 0 816 380 A1 | 7/1998 | C07K/14/52 |
| EP | 0 874 045 A1 | 10/1998 | |
| EP | 0 911 342 A1 | 4/1999 | |
| EP | 0 974 671 A1 | 1/2000 | |
| EP | 1 127 578 A1 | 8/2001 | |
| EP | 1 270 015 A2 | 1/2003 | |
| EP | 1 270 015 A3 | 2/2004 | |
| WO | 96/26217 | 8/1996 | |
| WO | 97/23614 | 7/1997 | |
| WO | WO 98/46211 | 10/1998 | A61K/9/16 |
| WO | 99/15691 | 4/1999 | |
| WO | WO 01/03719 A3 | 1/2001 | |
| WO | WO 01/03719 A2 | 1/2001 | |
| WO | WO 01/17543 A2 | 3/2001 | |
| WO | WO 01/17543 A3 | 3/2001 | |
| WO | WO 01/44472 A1 | 6/2001 | |
| WO | 03/074084 | 9/2003 | |

OTHER PUBLICATIONS

Supplementary Partial European Search Report, European Application No. EP 99 95 2793 (European Published Application No. EP 1 127 578 A1) (Oct. 27, 2004).
J. Body, "Current and Future Directions in Medical Therapy: Hypercalcemia", *CANCER Supplement*, 88 (12):3054–3058 (2000).
E. Romas et al., "Involvement of Receptor Activator of NFκB Ligand and Tumor Necrosis Factor–α in Bone Destruction in Rheumatoid Arthritis", *Bone*, 30(2):340–346 (2002).
B. Fautrel et al., "Cost of Illness Studies in Rheumatic Diseases", *Current Opinion in Rheumatology*, 14:121–126 (2002).
M. Iqbal et al., "Osteoporosis: A Review", *Missouri Medicine*, 99(1):19–24 (2002).
J. White et al., "Postmenopausal Hormone Replacement: Historical Perspectives and Current Concerns", *Clinical Excellence for Nurse Practitioners*, 4(5):277–285 (2000).
J. Green et al., "Renal Tolerability Profile of Novel, Potent Bisphosphonates in Two Short–Term Rat Models", *Pharmacology and Toxicology*, 80:225–230 (1997).
S. Porcel et al., "Anaphylaxis to calcitonin", *Allergologia et Immunopathologia*, 28(4), 243–245 (2000).
W. S. Simonet et al., "Osteoprotegerin: A Novel Secreted Protein Involved in the Regulation of Bone Density" *Cell*, 89:309–319 (1997).
Tomoyasu, et al., Characterization of Monomeric and Homodimeric Forms of Osteoclastogenesis Inhibitory Factor, Biochemical and Biophysical Research Communications 23, 382–387 (1998).

(Continued)

Primary Examiner—Jon Weber
Assistant Examiner—Chih-Min Kam
(74) Attorney, Agent, or Firm—Arnold & Porter LLP (57) ABSTRACT

A novel bone-pathobolism treating agent is provided. A bone-pathobolism treating agent comprising at least one substance selected from the group consisting of osteoclastogenesis inhibitory factor (OCIF), its homologs, and its variants, and a polysaccharide or its derivatives. As the polysaccharide or its derivatives, heparin, dextran sulfate and the like can be used. A bone-pathobolism treating agent is provided which has excellent therapeutic effect on bone-pathobolism such as osteoporosis, hypercalcemia, or chronic articular rheumatism and persistance of the activity. The agent is useful as a medicine.

30 Claims, 8 Drawing Sheets

OTHER PUBLICATIONS

Yamamoto, et al., Hypocalcemic Effect of Osteoclastogenesis Inhibitory Factor/Osteoprotegerin in the Thyroparathyroidectomized Rat, Endocrinology vol. 139, No. 9 (1998), p. 4012–4015.

Chowdhury, et al., Effects of Heparin on Osteoclast Activity, Journal of Bone and Mineral Research, vol. 7, No. 7, (1992), pp 771–777.

Cochran and Abernathy, Modulation of Bone Resorption by Glycosaminoglycans: Effects of Parathyroid Hormone and Interleukin–1, Bone, 9, 331–335 (1988).

Nobuyuki, et al., Remedy for Osteopathy, Publication No. 62–201825 (1987). abstract only.

Chemical Abstracts vol. 123, p. 662, (1995).

* cited by examiner

BONE-PATHOBOLISM TREATING AGENT

The present application is a continuation of PCT/JP99/05963, filed Oct. 28, 1999, which claims the benefits of foreign priority from Japan Application No. 322874, filed Oct. 28, 1998.

TECHNICAL FIELD

The present invention relates to a novel bone-pathobolism treating agent having high activity and high persistence. The bone-pathobolism treating agent of the present invention has excellent therapeutic activity on bone-pathobolism such as osteoporosis, hypercalcemia, or chronic articular rheumatism and is useful as a medicine.

BACKGROUND ART

Bones not only have an ability of supporting the body but also function as the largest storage-organ of the calcium in the organism and 99% of the calcium present in the organism is accumulated in the bones. In addition, bones are always remodelled through opposite actions of bone resorption and bone formation. This plays an important role on the maintenance of homeostasis of serum calcium. It is known that the activation of osteoclasts which bear an important role in bone resorption causes excessive flow of calcium into blood from bones to break the homeostasis of calcium in blood and induces hypercalcemia. Hypercalcemia is a disease which occurs due to osteectopia of tumor and the number of patients who suffer from it is expected to increase so that development of a treating agent is desired to be created in a hurry. At present, calcitonin, its derivatives, and bisphosphonate derivatives are used as such hypercalcemia treating agents. However, their therapeutic effect is not satisfactory and development of novel drugs replacing them is desired.

On the other hand, it has been reported that osteoclastogenesis inhibitory factor (OCIF) (WO96/26217) known as a protein inhibiting differentiation of osteoclasts has a hypocalcemic action [Biochemical and Biophysical Research Communications, Vol. 245, pp382–387 (1998); Endocrinology, Vol. 139, pp4012–4015 (1998)]. OCIF is expected as a quite new agent treating hypercalcemia. However, since it is a protein, OCIF is metabolized rapidly in the organism. Accordingly, development of an OCIF-preparation which is safer and has more enhanced action has been desired.

DISCLOSURE OF THE INVENTION

Under the circumstances, the inventors of the present invention have made extensive investigation and as a result, they have found that the effect of OCIF on bone-pathobolism can be further increased by adding a polysaccharide to OCIF to form a preparation. Therefore, an object of the present invention is to provide a bone-pathobolism treating agent in which the effect of OCIF on bone-pathobolism has been further increased and the effect has been rendered persistent.

The present invention relates to a bone-pathobolism treating agent comprising both at least one substance selected from the group consisting of osteoclastogenesis inhibitory factor (OCIF), its homologs, and its variants, and a polysaccharide or its derivatives.

In the present invention, heparin is preferred as the above polysaccharide, and dextran sulfate is preferred as the above polysaccharide derivative.

According to the present invention, there is provided a therapeutic agent having excellent action on bone-pathobolism such as osteoporosis, hypercalcemia, or chronic articular rheumatism and persistence of the activity. The therapeutic agent is useful as a medicine.

The present invention relates to a method for increasing the activity of osteoclastogenesis inhibitory factor using a polysaccharide or its derivatives.

OCIF used in the present invention is natural type or recombinant type obtained by the method described in WO96/26217 and its origin is not particularly limited. But particularly preferred OCIF is human type OCIF. Such a natural or recombinant type OCIF includes a monomer type having a molecular weight of about 60 kDa and a dimer type having a molecular weight of about 120 kDa as measured by SDS-PAGE under non-reducing conditions.

In the present invention, analogs and variants of OCIF may be used. The homologs include those obtained by preparing a cDNA library using poly $(A)^+$ RNA from IMR-90 cell (ATCC CCL-186), obtaining cDNA of OCIF homolog by a hybridization method using OCIF cDNA fragment as a probe, inserting the cDNA into an expression vector, introducing the vector in a usually used host, expressing the cDNA in the host, and purifying the expressed protein by a conventional method. More specifically, the homologs include OCIF2, OCIF3, OCIF4, or OCIF5 as described in WO96/26217.

As described in WO96/26217, among these, OCIF2 has a deletion of 21 bp from the 265th guanine to the 285th guanine in the base sequence of OCIF cDNA and a deletion of 7 amino acids from the 68th glutamic acid (Glu) to the 74th glutamine (Gln) in the amino acid sequence.

OCIF3 has the same base sequence as the OCIF cDNA except for the followings. The 9th cytidine is replaced by guanine and the −19th asparagine (Asn) is replaced by lysine (Lys) in the amino acid sequence. However, this is the substitution of amino acids in the signal sequence and is considered to have no influence on OCIF3 to be secreted. Further, OCIF3 has a deletion of 117 bp from the 872nd guanine to the 988th guanine in the base sequence of OCIF cDNA and a deletion of 39 amino acids from the 270th threonine (Thr) to the 308th leucine (Leu) in the amino acid sequence.

OCIF4 has the same base sequence as OCIF cDNA except for the followings. The 9th citidine is replaced by guanine and the −19th asparagine (Asn) is replaced by lysine (Lys) in the amino acid sequence. The 22nd guanine is replaced by thymidine and the −14th alanine (Ala) is replaced by serine (Ser) in the amino acid sequence of OCIF. However, this is the substitution of amino acids in the signal sequence and is considered to have no influence on OCIF4 to be secreted. Further, there is an insertion of intron 2 of about 4 kb between the 400th and 401th in the base sequence of OCIF cDNA and the open reading frame is terminated therein. In the amino acid sequence, a novel amino acid sequence consisting of 21 amino acids is added after the 112th alanine (Ala) of the amino acid sequence of OCIF.

OCIF5 has the same base sequence as OCIF cDNA except for the followings. The 9th cytidine is replaced by guanine and the −19th asparagine (Asn) is replaced by lysine (Lys) in the amino aid sequence. However, this is the substitution of amino acids in the signal sequence and is considered to have no influence on OCIF5 to be secreted. Further, there is an insertion of the latter half of intron 2 of about 1.8 kb between the 400th and 401th in the base sequence of OCIF cDNA and the open reading frame is terminated therein. In the amino acid sequence, a novel amino acid sequence consisting of 12 amino acids is added after the 112th alanine (Ala) of the amino acid sequence of OCIF.

The variants include those in which one or more amino acids have been inserted in, added to, substituted in, or deleted of the amino acid sequence of OCIF. More specifically, the variants include those obtained by preparing OCIF variant cDNA by introducing substitution or deletion mutation by a PCR method or cleavage with a restriction enzyme, inserting the cDNA into an expression vector, incorporating the vector into a usually used host, expressing the cDNA in the host and purifying the expressed protein by a conventional method.

The polysaccharide used in the present invention is a polymer (glucan) formed through glycoside bonding of monosaccharides and is preferably a heteropolysaccharide (heteroglycan) having 2 or more constituent monosaccharides. More specifically, the polysaccharide which can be used include natural polysaccharides such as hyaluronic acid, chondroitin sulfate, dermatan sulfate, heparan sulfate, keratan sulfate, carrageenan, pectin, and heparin, synthetic polysaccharides such as dextran, and synthetic polysaccharide derivatives such as dextran sulfate. Particularly preferably, sulfate ester of glucan is used. For example, heparin having a molecular weight of 3,000 to 6,000 or dextran sulfate having a molecular weight of 5,000 to 10,000 is used. The bone-pathobolism treating agent of the present invention is preferably a combination of at least one substance selected from the group consisting of OCIF, its homologs, and its variants and a polysaccharide or its derivatives in a proportion of 1 to 100 folds, particularly 1 to 16 folds in an amount of the polysaccharide or its derivatives to the OCIF, its derivatives, or variants. The preparation of the present invention comprising a combination of at least one substance selected from the group consisting of OCIF, its analogs, and its variants and a polysaccharide or its derivatives is a bone-pathobolism treating agent having excellent persistence and therapeutic effect as compared with administration of OCIF alone and is effective on bone-pathobolisms such as osteoporosis, hypercalcemia, chronic articular rheumatism.

The preparation of the present invention is safely administered orally or parenterally to humans or animals as a medicine. Parenteral administration includes intravenous injection, intramuscular injection, subcutaneous injection, nasal administration, intraoral administration, permucomembraneous administration, etc. The preparations to be administered by these administration routes can be formulated by a known pharmaceutical production method, and administered together with pharmacologically acceptable vehicles, excipients, lubricants, colorants, etc. as a preparation of a medical composition. When an injection is prepared, OCIF and a polysaccharide, optionally a pH adjuster, a buffer, a stabilizer, a solubilizer, etc. are added to form injections by a conventional method. In this case, known additives such as human serum albumin and a surfactant may be used in combination. As the surfactant, polyanions and anionic surfactants are cited. The injection can be dispensed in vials to form a solution preparation or prepared as a freeze-dried preparation which upon use is dissolved in distilled water, physiological saline or the like at appropriate timing. Upon administering OCIF to normal rats once a day for continuous 2 weeks in a dose of 3 or 24 mg/kg·day, increases in bone density and amount, respectively, were observed but no histopathological disorder in 38 tissues nor change in blood was observed [H. Yasuda et al.: Endocrinology, Vol. 139, pp1329–1337 (1998)]. Thus, the action of OCIF is highly specific to bone and it is expected that OCIF can be administered safely to humans.

The amount and method of administration of the bone-pathobolism treating agent of the present invention to patients are not limited particularly, since they may vary depending on the severity of symptom, age, condition of body, and body weight of the patient. For example, the agent may be parenterally administered once to several times a day in a dose of about 0.01 to 1 mg/kg per day for adults. The activity of the preparation of the present invention can be performed by measuring the concentration of serum calcium. For example, OCIF solution prepared with a suitable solvent and being added a polysaccharide is intravenously administered to a rat, blood is collected on time, and the serum calcium level is measured by a conventional method.

The present invention relates to a method for elevating the activity of osteoclastogenesis inhibitory factor by use of a polysaccharide or its derivatives. According to the present invention, the blood level of OCIF can be elevated to enhance the action of OCIF lowering the serum calcium level.

BRIEF DESCRIPTION OF THE DRAWINGS

[Explanation of Symbols]
□: Administration of 0.5 mg/kg OCIF alone
◇: 0.5 mg/kg OCIF+0.5% dextran sulfate
○: 0.5 mg/kg OCIF+0.5% apple pectin
Δ: 0.5 mg/kg OCIF+0.5% citrus pectin

[Explanation of Symbols]
□: Administration of 0.5 mg/kg OCIF alone
◇: 0.5 mg/kg OCIF+0.5% dextran sulfate
○: 0.5 mg/kg OCIF+0.5% apple pectin
Δ: 0.5 mg/kg OCIF+0.5% carrageenan (lambda)

[Explanation of Symbols]
○: Administration of 50 $\mu$g/kg OCIF alone
Δ: 50 $\mu$g/kg OCIF+0.1% dextran sulfate
□: 50 $\mu$g/kg OCIF+0.15% apple pectin

[Explanation of Symbols]
○: Administration of 1 mg/kg OCIF alone
Δ: 1 mg/kg OCIF+0.1% dextran sulfate
□: 1 mg/kg OCIF+0.15% apple pectin

BEST MODE FOR CARRYING OUT THE INVENTION

EXAMPLES

The following examples are presented in order to more specifically explain the present invention by examples. However, they are only concrete illustrations and the present invention is by no means limited thereto.

Example 1

Production of Injections—1

500 $\mu$g of human OCIF obtained by the method described in WO96/26217 and 2 mg of heparin were dissolved in 5 ml of 10 mM sodium phosphate buffer solution (pH 7.0) containing 0.15 M NaCl and 0.01% Tween 80, and the resulting solution was sterilized by passing through a 0.22 $\mu$m sterile filter (Millex GV, Millipore Co.) and then packed in a vial to obtain injections for intravenous injection.

Production of Injections—2

500 $\mu$g of human OCIF obtained by the method described in WO96/26217 and 2 mg of dextran sulfate were dissolved in 5 ml of 10 mM sodium phosphate buffer solution (pH 7.0) containing 0.15 M NaCl and 0.01% Tween 80 and the resulting solution was sterilized by passing through a 0.22 $\mu$m sterile filter (Millex GV, Millipore Co.) and then packed in a vial to obtain injections for intravenous injection.

Example 2

Hypocalcemic Effect of OCIF by the Addition of a Polysaccharide—1

Figure 1:
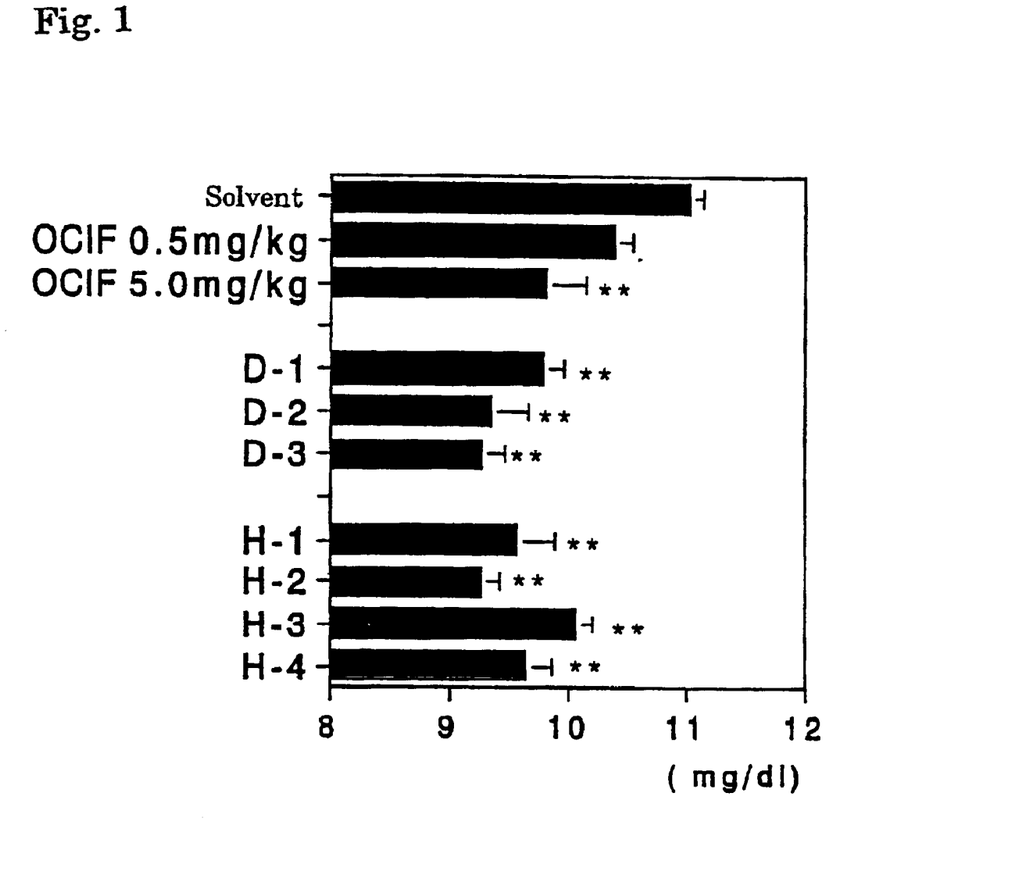
FIG. 1 shows serum calcium level after 3 hours from the administration of the preparation containing OCIF and a polysaccharide in Example 2.
[Explanation of Symbols]
D-1: 0.5 mg/kg OCIF+2 mg/kg dextran sulfate (molecular weight 5,000)
D-2: 0.5 mg/kg OCIF+2 mg/kg dextran sulfate (molecular weight 8,000)
D-3: 0.5 mg/kg OCIF+2 mg/kg dextran sulfate (molecular weight 10,000)
H-1: 0.5 mg/kg OCIF+2 mg/kg heparin (207.8 units/mg)
H-2: 0.5 mg/kg OCIF+2 mg/kg heparin (171.2 units/mg)
H-3: 0.5 mg/kg OCIF+2 mg/kg heparin (molecular weight 3,000)
H-4: 0.5 mg/kg OCIF+2 mg/kg heparin (molecular weight 6,000)
**: Significant (p values$\leq$1%)

To 2 ml of 0.25 mg/ml human OCIF solution prepared by dissolving human OCIF (of dimer type) (recombinant type OCIF obtained by the method described in WO96/26217) in 10 mM sodium phosphate buffer solution (pH 7.0) containing 0.15 M NaCl and 0.01% Tween 80 (hereafter, referred to as a solvent), 2 mg of dextran sulfate (molecular weight 8,000 or 10,000: Sigma AB, and molecular weight 5,000 or 50,000: Wako Pure Chemical Industry Co., Ltd.), or heparin (207.8 or 171.2 unit/mg: Wako Pure Chemical Industry Co., Ltd. and molecular weight 3,000 or 6,000: Sigma AB) was dissolved and then the solution was incubated at 4° C. for a day. At the same time, 0.25 and 2.5 mg/ml human type OCIF solutions and the solvent were incubated at 4° C. for a day similarly. These test sample solutions were provided as OCIF+dextran sulfate administered group (D group), OCIF+heparin administered group (H group) (D group and H group were administered with 0.5 mg/kg OCIF), OCIF alone administered group (administered with 0.5 mg/kg and 5 mg/kg OCIF, respectively), and solvent administered group. Four weeks age female Wistar rats were once intravenously administered with the samples at a dose of 2 ml/kg. After 3 hours from the administration, blood was collected from the eyehole to prepare serum. The calcium level in the obtained serum was measured using Calcium C Test (Wako Pure Chemical Industry Co., Ltd.). FIG. 1 shows the results. As a result, it was observed that the administration of 0.5 mg/kg of human OCIF to which one of various types of dextran sulfate or heparin has been added exhibited a significant enhancing effect in hypocalcemic action. Therefore, it was confirmed that the addition of a polysaccharide can enhance hypocalcemic action of human OCIF.

Example 3

Effect of the Amount of Added Polysaccharide on Enhancement of the OCIF-action

In 2 ml of the 0.25 mg/ml human OCIF solutions prepared in the same manner as in Example 2, dextran sulfate (molecular weight 5,000: Wako Pure Chemical Industry Co., Ltd.) was dissolved in a proportion of 1, 2, 4, 8, or 16 folds in weight, based on the amount of OCIF respectively, and the mixtures were incubated at 4° C. for a day. Similarly, heparin (207.8 units/mg: Wako Pure Chemical Industry Co., Ltd.) was dissolved in 2 ml of 0.25 mg/ml human OCIF solutions in the same proportion and the mixtures were incubated at 4° C. for a day.

Figure 2:
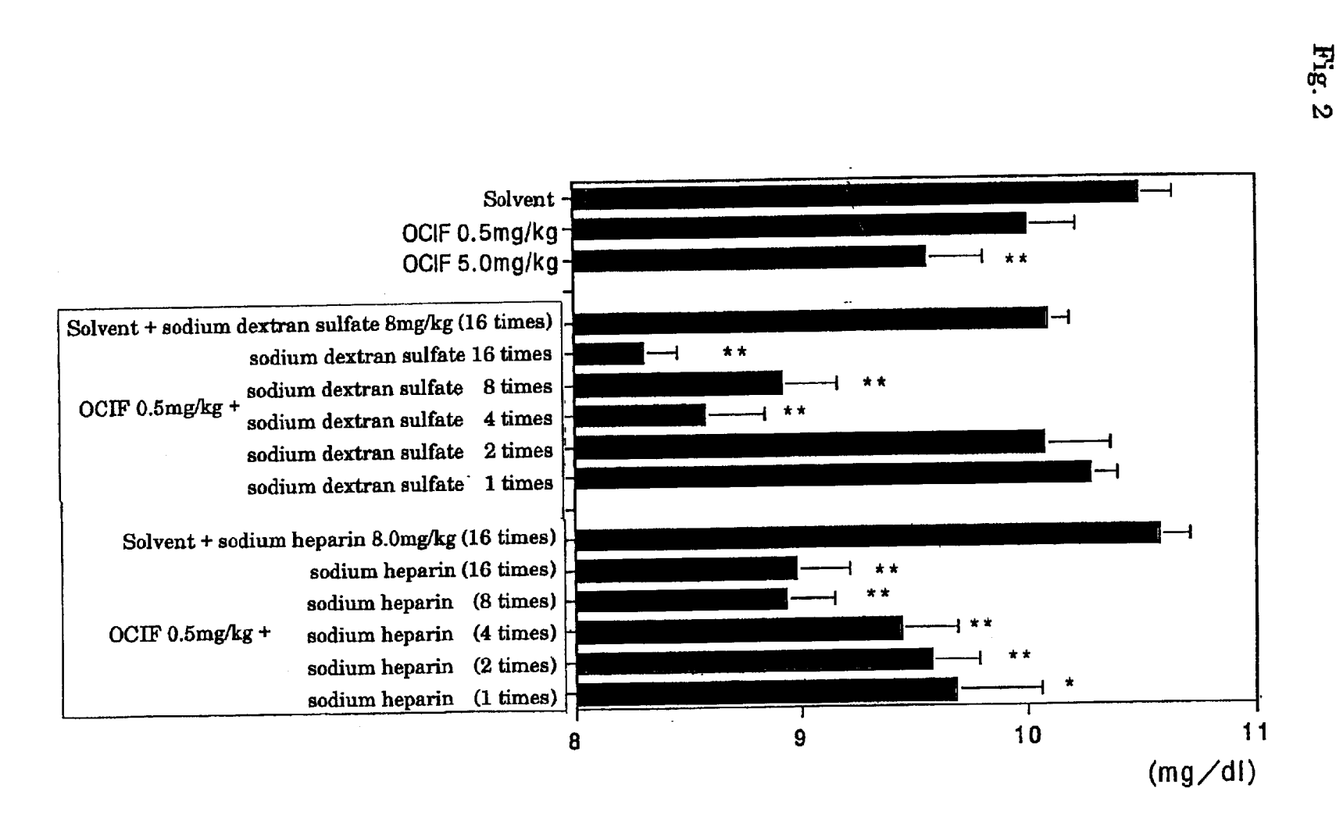
FIG. 2 shows serum calcium level after 3 hours from the administration of OCIF and polysaccharide with various mixing ratios in Example 3.
[Explanation of Symbols]
**: Significant (p values$\leq$1%)

Further, 4 mg/ml dextran sulfate or heparin solution, 0.25 and 2.5 mg/ml human OCIF solutions, and the solvent alone were similarly incubated at 4° C. for a day. These test sample solutions were once intravenously administered to four weeks age female Wistar rats at a dose of 2 ml/kg. After 3 hours from the administration, blood was collected from the eyehole to prepare serum. The calcium level in the obtained serum was measured using Calcium C Test (Wako Pure Chemical Industry Co., Ltd.). The kit is constructed based on a chelate method (orthocresol phthalein coplexon (OCPC) method) in which the effect of magnesium is removed and specificity is increased with the addition of 8-quinolinol. Calcium give rises purple red color upon binding to OCPC under alkaline conditions. Measurement of absorbance enables assessment of calcium concentration. FIG. 2 shows the results. As a result, significant hypocalcemic action was recognized when dextran sulfate was added 4 folds as much as human OCIF or more. Significant hypocalcemic action was also seen when an equivalent amount of heparin was added to human OCIF. Therefore, it was confirmed that simultaneous administration of human OCIF and a polysaccharide in specific proportions can further enhance the hypocalcemic action of OCIF.

Figure 3:
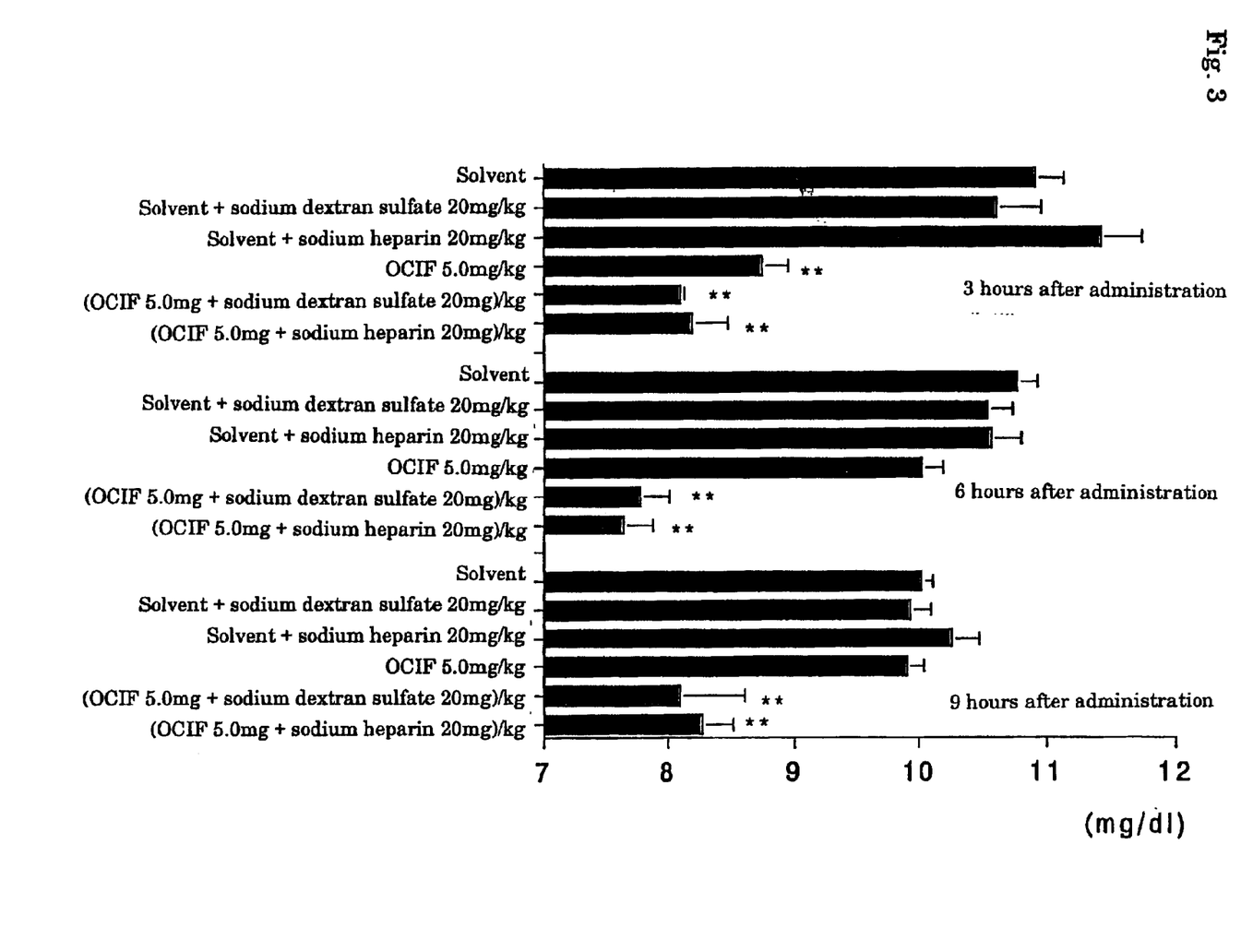
FIG. 3 shows serum calcium level after 3, 6, and 9 hours, respectively, from the administration of the preparation containing OCIF and a polysaccharide in Example 4.
[Explanation of Symbols]
**: Significant (p values$\leq$1%)

Example 4
Enhancing Effect on Persistence of OCIF by the Addition of a Polysaccharide After dissolving 20 mg of dextran sulfate (molecular weight 5,000: Wako Pure Chemical Industry Co., Ltd.) in 2 ml of 2.5 mg/ml human OCIF solution prepared with the solvent, the mixture was incubated at 4° C. for a day. Twenty mg heparin (207.8 units/mg: Wako Pure Chemical Industry Co., Ltd.) was also dissolved in 2 ml of the 2.5 mg/ml human OCIF solution and similarly incubated at 4° C. for a day. Further, 2.5 mg/ml human OCIF solution and the solvent were incubated at 4° C. for a day. Four weeks age female Wistar rats were intravenously administered with the test sample solutions at a dose of 2 ml/kg (5 mg/kg as the amount of OCIF) respectively. After 3, 6, and 9 hours from the administration, blood was collected from the eyehole to prepare serum. The calcium level in the obtained serum was measured using Calcium C Test (Wako Pure Chemical Industry Co., Ltd.). FIG. 3 shows the results. As a result, a significant decrease in serum calcium level was observed in the group administered with 5 mg/kg human OCIF solution alone after 3 hours from the administration, but no significant hypocalcemic action was observed after 6 and 9 hours, respectively, after the administration.

On the other hand, 2.5 mg/ml human OCIF solution to which dextran sulfate or heparin was added, respectively, in amounts 4 folds as much as human OCIF had a significant hypocalcemic effect even after 9 hours from the administration. Therefore, it was confirmed that the simultaneous addition of human OCIF and a polysaccharide can give persistence enhancing effect.

Example 5
Enhancing Effect of Added Polysaccharides on the Persistence of Circulating OCIF level—1

Figure 4:
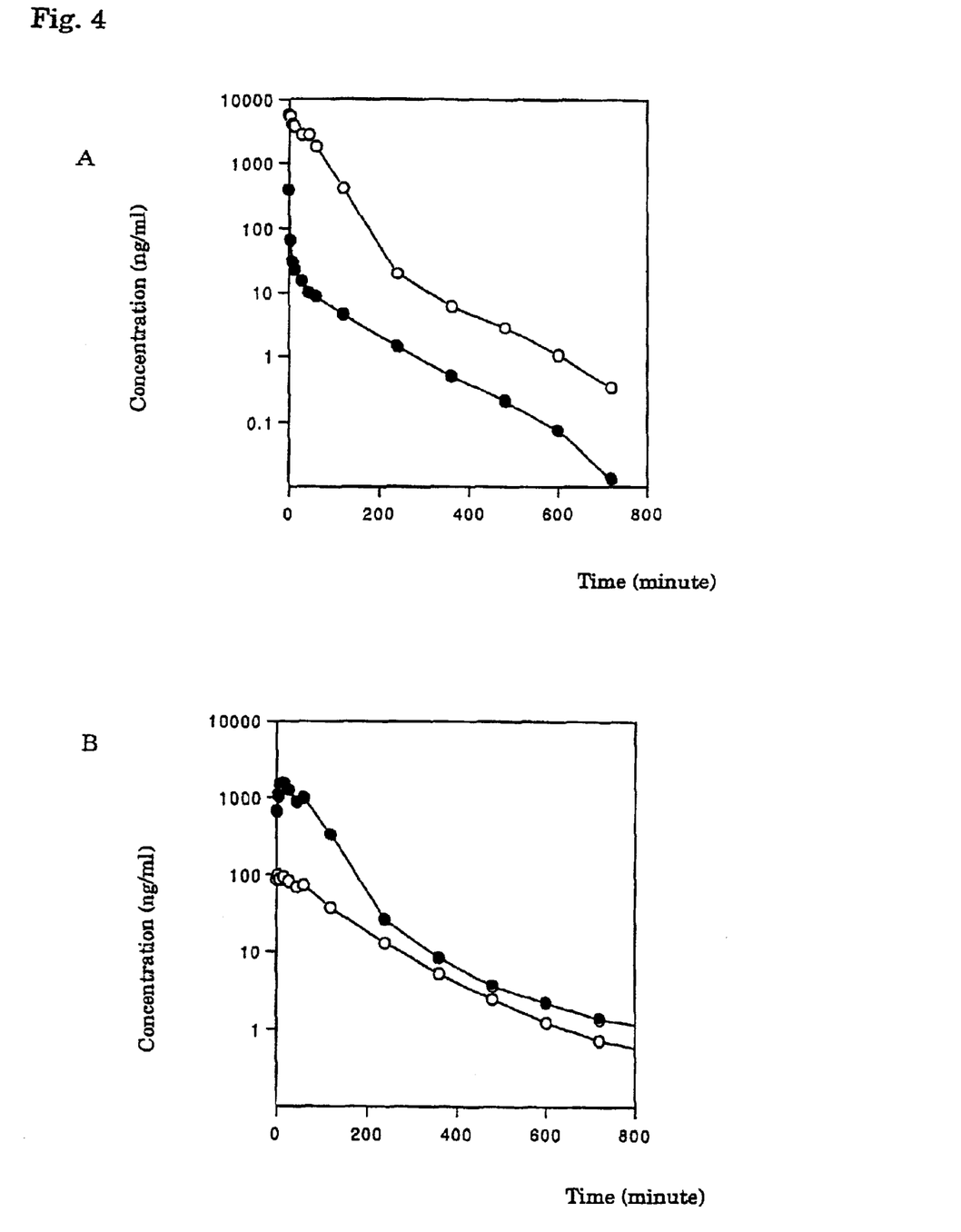
FIGS. 4A and 4B show time-dependent change in blood OCIF level when a preparation containing OCIF and a polysaccharide was administered in Example 5.
[Explanation of Symbols]
A: A figure illustrating the blood level of dimer type OCIF.
B: A figure illustrating the blood level of monomer type OCIF.
●: OCIF
○: OCIF+dextran sulfate
Figure 5:
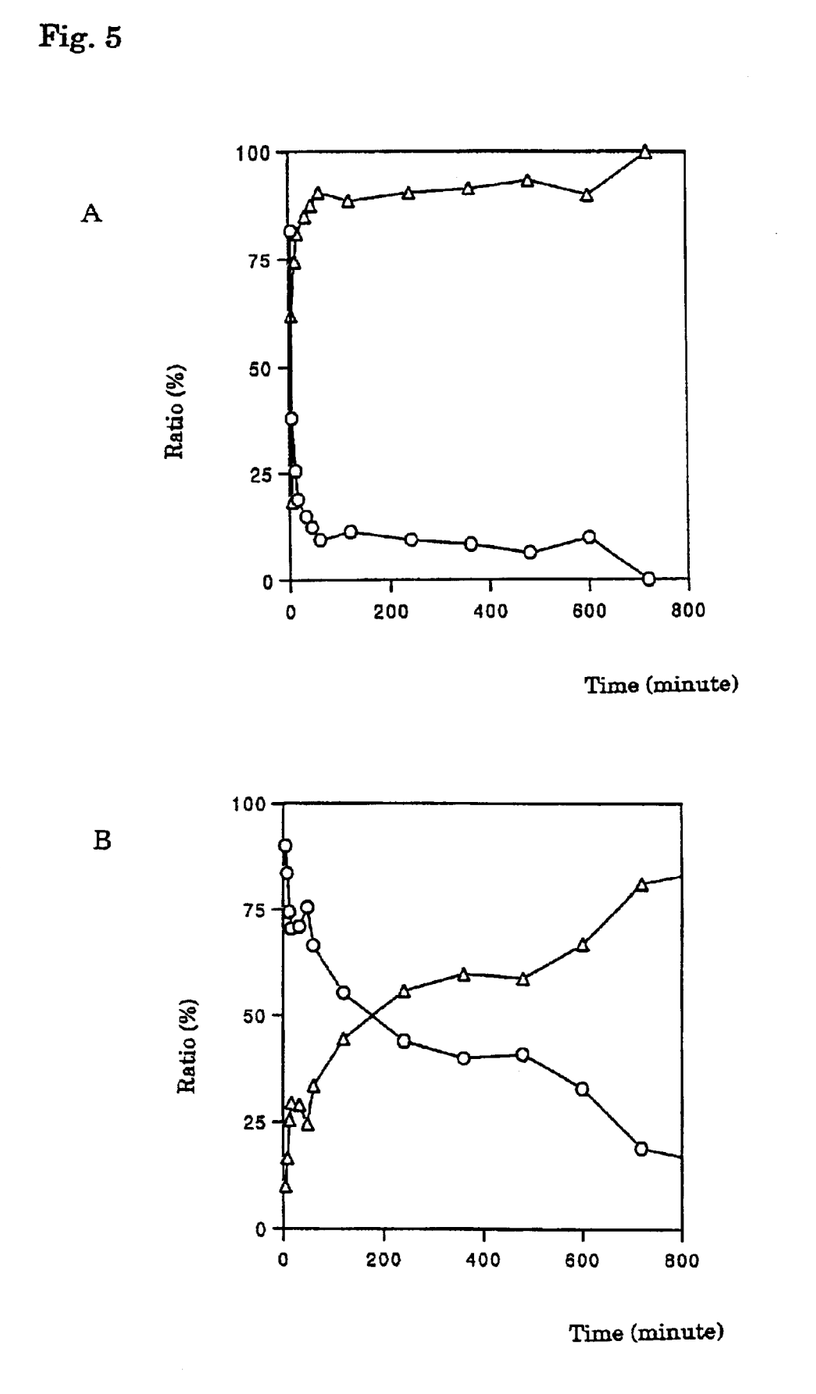
FIGS. 5A and 5B shows time-dependent change in the proportion of monomer type OCIF/dimer type OCIF in blood when a preparation containing OCIF and a polysaccharide was administered in Example 5.
[Explanation of Symbols]
A: OCIF
B: OCIF+dextran sulfate
O: Dimer type OCIF
Δ: Monomer type OCIF

To 1 ml of the 1 mg/ml human OCIF solution prepared in the same manner as in Example 2, 1 ml of 4 mg/ml of dextran sulfate was added and the obtained mixture was incubated at 4° C. for a day. The test sample solution was intravenously administered to 9 weeks age male Wistar rats at a dose of 1 ml/kg. After 2, 5, 10, 15, 30, 45, 60, 120, 240, 360, 480, 600, 720, and 1440 minutes from the administration, blood was collected from the eyehole to prepare serum. The human OCIF level in the obtained serum was measured by the ELISA described in WO96/26217 using monoclonal antibodies capable of recognizing dimer type OCIF, monoclonal antibodies capable of recognizing monomer type OCIF (Biochemical and Biophysical Research Communications, Vol. 245, pp382–387 (1998)). The total OCIF level was calculated as the sum of the dimer type OCIF level and monomer type OCIF level. FIGS. 4 and 5 show the results. As a result, as compared with the group administered with 500 µg/kg human OCIF alone, the group administered with the human OCIF solution to which dextran sulfate 4 folds as much as the human OCIF was added maintained evidently high circulating OCIF level (FIG. 4). It was confirmed that the conversion of dimer type OCIF to monomer type OCIF in blood was inhibited (FIG. 5). Therefore, the addition of a polysaccharide enables circulating OCIF level, in particular the circulating level of dimer type OCIF having high hypocalcemic activity (Biochemical and Biophysical Research Communications, Vol. 245, pp382–387 (1998)), to persist.

Example 6
Enhancing Effect of Added Polysaccharides on the Persistence of Circulating OCIF level—2

Figure 6:
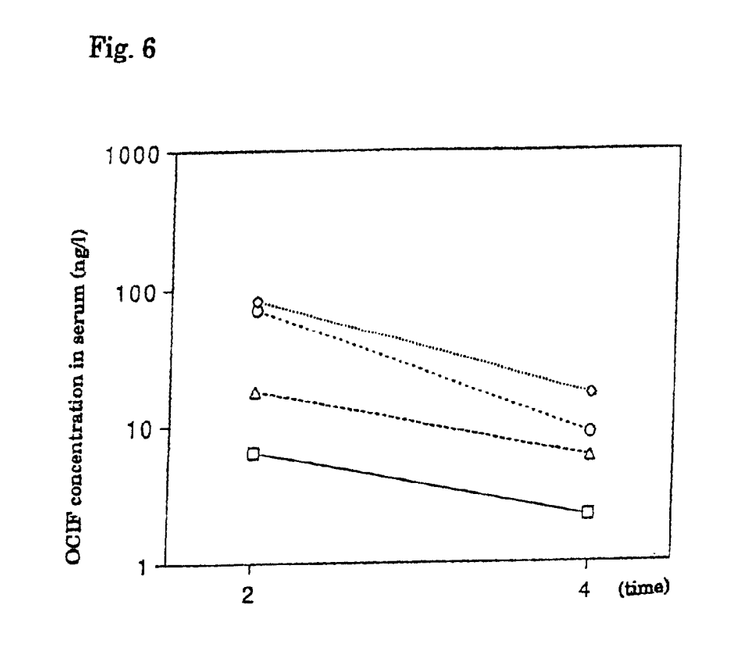
FIG. 6 shows blood OCIF level after 2 and 4 hours from the administration of a preparation containing OCIF and a polysaccharide (dextran sulfate, apple pectin, or citrus pectin) in Example 6.

To 2 ml of the 0.25 mg/ml human OCIF solution prepared in the same manner as in Example 2, equivalent volume of 0.5% solution [solvent: 10 mM sodium phosphate buffer solution (pH 7.0) containing 0.15 M NaCl, 0.01% polysorbate 80] of dextran sulfate, apple pectin, or a citrus pectin (all the products of Wako Pure Chemical Industry Co., Ltd.) and the obtained mixture was incubated at room temperature for 4 hours to prepare a test sample solution. As a control, 0.25 mg/ml OCIF solution (2 ml) alone was mixed with the equivalent volume of the solvent similarly and the mixture was incubated at room temperature for 4 hours. These test sample solutions were intravenously administered to 4 weeks age male Wistar rats at a dose of 2 ml/kg. After 2 and 4 hours from the administration, blood was collected from the eyehole under etherization to prepare serum. The human OCIF level in the obtained serum was measured by the ELISA described in WO96/26217. FIG. 6 shows the results.

Figure 7:
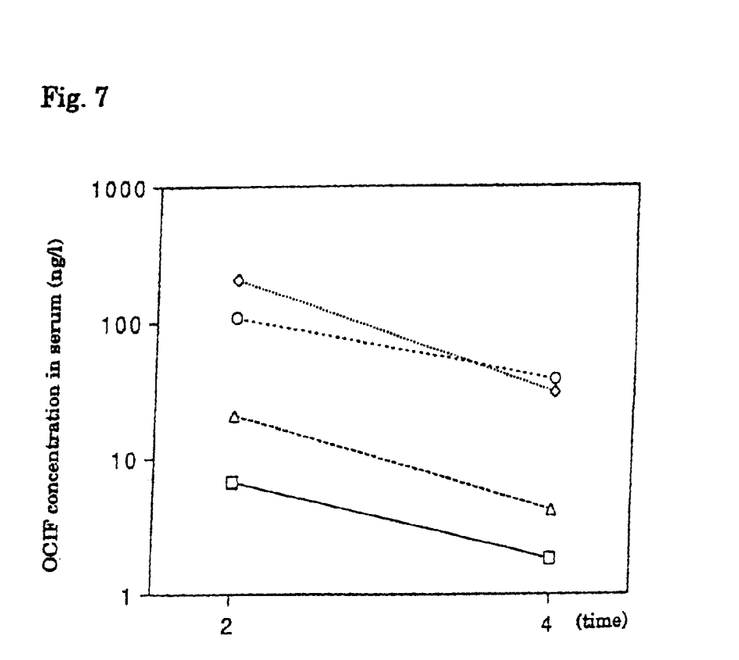
FIG. 7 shows the blood OCIF level after 2 and 4 hours from the administration of a preparation containing OCIF and a polysaccharide (dextran sulfate, apple pectin, or carrageenan) in Example 6.

In the same manner as above, 2 ml of 0.25 mg/ml human OCIF solution was mixed with 0.5% solution of dextran sulfate, apple pectin, or carrageenan (lambda) (all products of Wako Pure Chemical Industry Co., Ltd.) and the mixture was incubated at room temperature for 4 hours to prepare test sample solutions. As a control, 0.25 mg/ml OCIF solution alone was similarly mixed with the equivalent volume of the solvent and the mixture was incubated at room temperature for 4 hours. These test sample solutions were intravenously administered to 4 weeks age male Wistar rats at a dose of 2 ml/kg. After 2 and 4 hours from the administration, blood was collected from the eyehole under etherization to prepare serum. The human OCIF level in the obtained serum was measured by the ELISA described in WO96/26217. FIG. 7 shows the results.

As a result, as compared with the group administered with the human OCIF solution alone, each of the groups administered with the test sample solution to which dextran sulfate, apple pectin, and citrus pectin was added, respectively, maintained evidently high circulating OCIF level (FIG. 6). The group administered with the test sample solution being added carrageenan apparently maintained high circulating OCIF level similarly (FIG. 7). Therefore, it was confirmed that the addition of the polysaccharides enables the circulating OCIF level to persist.

Figure 8:
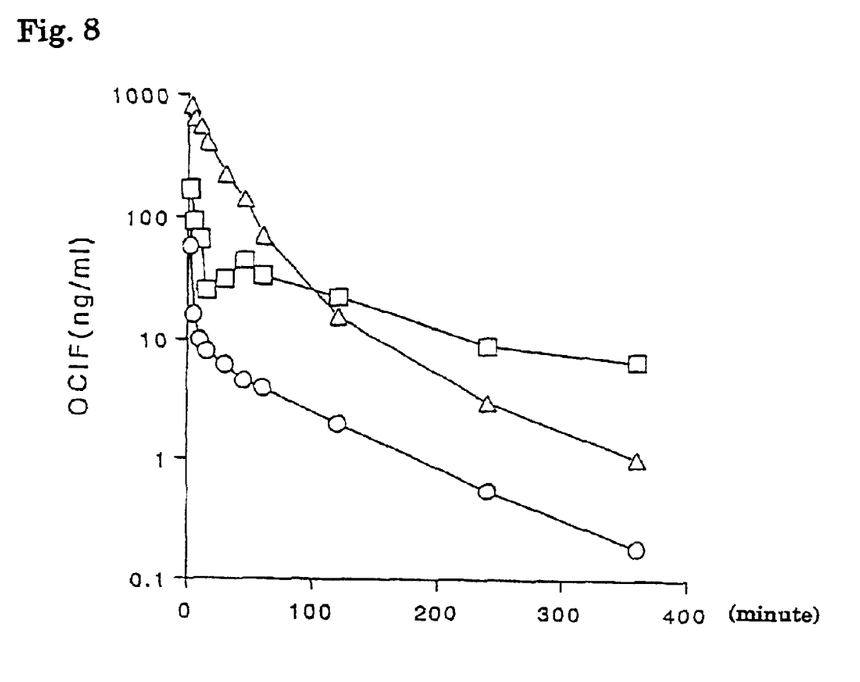
FIG. 8 shows the blood OCIF level after intravenous administration of a preparation containing OCIF and a polysaccharide (dextran sulfate or apple pectin) in Example 7.
Figure 9:
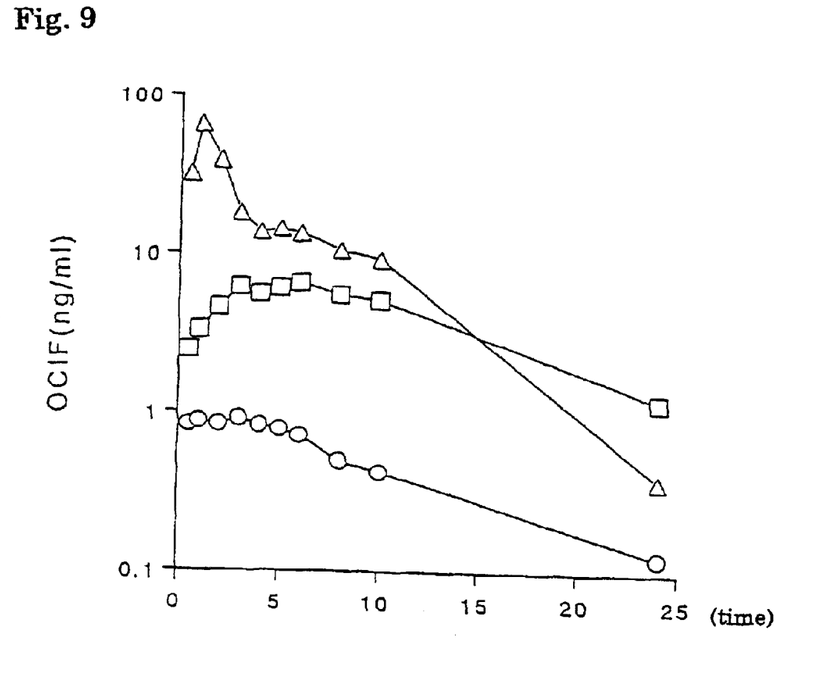
FIG. 9 shows the blood OCIF level after the intramuscular administration of a preparation containing OCIF and a polysaccharide (dextran sulfate or apple pectin) in Example 7.

Example 7
Enhancing Effect of Added Polysaccharides on the Persistence of Circulating OCIF Level Using dextran sulfate or apple pectin (Wako Pure Chemical Industry Co., Ltd.) as a polysaccharide, difference in persistence effect on circulating OCIF due to difference in administration route was studied. OCIF solutions diluted with a solvent [10 mM sodium phosphate buffer solution (pH 7.0) containing 0.15 M NaCl and 0.01% Polysorbate 80] to 50 µg/ml for intravenous administration and to 1,000 µg/ml for intramuscular administration were prepared. To these solutions the above polysaccharides were added respectively, to obtain test sample solutions. In this case, dextran sulfate was added to the OCIF solutions for intravenous and for intramuscular administration each in a concentration of 0.1%. Apple pectin was dissolved in the solvent to prepare 3 mg/ml solution and the solution was mixed with the same volume of the OCIF solution (containing 100 µg/ml and 2,000 µg/ml OCIF, respectively), for intravenous administration or intramuscular administration. The respective solutions were administered to 4 weeks age male Wistar rats at a dose of 1 ml/kg. Blood was collected from the eyehole under etherization to prepare serum after 2, 5, 10, 15, 30, 45, 60, 120, 240, and 360 minutes from the administration for the intravenous administration, and after 30 minutes, 1, 2, 3, 4, 5, 6, 8, 10, and 24 hours from the administration for the intramuscular administration. The OCIF level in the obtained serum was measured by the ELISA described in WO96/26217. FIGS. 8 and 9 show the results.

As a result, in the intravenous administration (FIG. 8) and intramuscular administration (FIG. 9) of the OCIF solutions to which dextran sulfate or apple pectin was added respectively, evidently high circulating OCIF level was maintained. Therefore, it was confirmed that the addition of these polysaccharides enables the circulating OCIF level to be maintained and the enhancing effect on the persisstence of OCIF level is observed regardless of the administration route.

Example 8

Hypocalcemic Effect of OCIF by the Addition of a Polysaccharide—2

Figure 10:
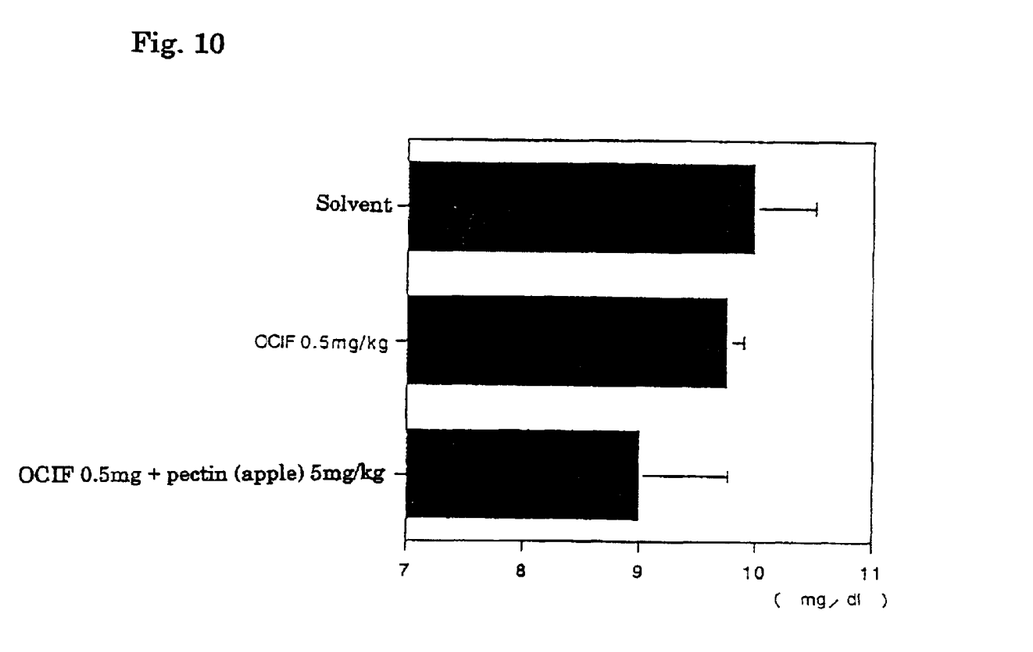
FIG. 10 shows the serum calcium level after 4 hours from the administration of a preparation containing OCIF and a polysaccharide (apple pectin) in Example 8.

To 2 ml of the 0.25 mg/ml human OCIF solution prepared in the same manner as in Example 2 was mixed with an equivalent volume of 0.5% apple pection (Wako Pure Chemical Industry Co., Ltd.) solution [solvent: 10 mM sodium phosphate buffer solution (pH 7.0) containing 0.15 M NaCl, 0.01% Polysorbate 80] and the obtained mixture was incubated at room temperature for 4 hours to prepare a test sample solution. At the same time, a mixture solution of equal volume of OCIF solution (2 ml of the 0.25 mg/ml human OCIF) and the solvent, and the solvent alone were provided. The respective test sample solutions were intravenously administered to 4 weeks age male Wistar rats at a dose of 2 ml/kg. After 4 hours from the administration, blood was collected from the eyehole under etherization to prepare serum. The OCIF level in the obtained serum was measured using Calcium C Test (Wako Pure Chemical Industry Co., Ltd.). FIG. 10 shows the results. As a result, the group administered with the 0.5 mg/kg human OCIF solution alone showed no hypoclcemic effect but in the group administered with the 0.5 mg/kg human type OCIF to which apple pectin was added, significant hypocalmic effect was observed. Therefore, it was confirmed that the addition of the polysaccharides enhances the hypocalcemic action of human type OCIF.

INDUSTRIAL APPLICABILITY

According to the present invention, there is provided a bone-pathobolism treating agent comprising at least one substance selected from the group consisting of osteoclastogenesis inhibitory factor, its homologs, and its variants and a polysaccharide or its derivatives. According to the present invention, there is provided a therapeutic agent having excellent effect on bone-pathobolism such as osteoporosis, hypercalcemia, or chronic articular rheumatism and persistence of the activity. The therapeutic agent is useful as a medicine.

What is claimed is:

1. A method for enhancing the activity of a human osteoclastogenesis inhibitory factor (OCIF) protein said method comprising administering an effective amount of said human OCIF protein to a subject in need thereof in conjunction with an activity enhancing amount of a polysaccharide selected from the group consisting of: hyaluronic acid, chondroitin sulfate, dermatan sulfate, heparan sulfate, keratan sulfate, carrageenan, pectin, heparin, dextran, dextran sulfate, and sulfated glucan;
wherein the activity of said human OCIF protein, administered with said polysaccharide, is enhanced relative to the activity of said human OCIF protein when administered in the absence of said polysaccharide.

2. The method of claim 1, wherein said method comprises administering an effective amount of said human OCIF protein to a subject in need thereof in conjunction with an activity enhancing amount of a polysaccharide selected from the group consisting of: hyaluronic acid, chondroitin sulfate, dermatan sulfate, heparan sulfate, keratan sulfate, carrageenan, pectin, heparin, dextran, dextran sulfate, and sulfated glucan, in the form of a medicinal composition comprising said human OCIF protein and said polysaccharide.

3. The method of claim 1, wherein said polysaccharide is selected from the group consisting of: heparin, pectin, carrageenan, and dextran sulfate.

4. The method of claim 1, wherein said polysaccharide is selected from the group consisting of: heparin having a molecular weight of 3,000 to 6,000, and dextran sulfate having a molecular weight of 5,000 to 10,000.

5. The method of claim 1, wherein the weight ratio of human OCIF protein to polysaccharide is at least about 1:4.

6. The method of claim 1, wherein said OCIF protein is lyophilized.

7. A method for enhancing the activity of a human osteoclastogenesis inhibitory factor (OCIF) protein homolog selected from the group consisting of human OCIF2, human OCIF3, human OCIF4, and human OCIF5, said method comprising administering an effective amount of said human OCIF protein homolog to a subject in need thereof in conjunction with an activity enhancing amount of a polysaccharide selected from the group consisting of: hyaluronic acid, chondroitin sulfate, dermatan sulfate, heparan sulfate, keratan sulfate, carrageenan, pectin, heparin, dextran, dextran sulfate, and sulfated glucan;
wherein the activity of said human OCIF protein homolog administered with said polysaccharide is enhanced relative to the activity of said human OCIF protein homolog when administered in the absence of said polysaccharide.

8. A method of treating a bone-pathobolism selected from the group consisting of: osteoporosis, hypercalcemia and chronic articular rheumatism comprising administering to a subject in need thereof a composition comprising an amount of human osteoclastogenesis inhibitory factor (OCIF) protein and a polysaccharide, effective in combination for increasing bone density; wherein the polysaccharide is selected from the group consisting of: hyaluronic acid, chondroitin sulfate, dermatan sulfate, heparan sulfate, keratan sulfate, carrageenan, pectin, heparin, dextran, dextran sulfate, and sulfated glucan; thereby increasing the subjects bone density.

9. The method of claim 8, wherein said polysaccharide is selected from the group consisting of: heparin, pectin, carrageenan, and dextran sulfate.

10. The method of claim 8, wherein said polysaccharide is selected from the group consisting of: heparin having a molecular weight of 3,000 to 6,000, and dextran sulfate having a molecular weight of 5,000 to 10,000.

11. The method of claim 8, wherein the weight ratio of human OCIF protein to polysaccharide in said composition is at least about 1:4.

12. The method of claim 8, wherein said OCIF protein is lyophilized.

13. A method of treating a bone-pathobolism selected from the group consisting of: osteoporosis, hypercalcemia and chronic articular rheumatism comprising administering to a subject in need thereof a composition comprising an amount of a human osteoclastogenesis inhibitory factor (OCIF) protein homolog and a polysaccharide, effective in combination for increasing bone density; wherein said OCIF protein homolog is selected from the group consisting of: human OCIF2, human OCIF3, human OCIF4, and human OCIF5; and wherein said polysaccharide is selected from the group consisting of: hyaluronic acid, chondroitin sulfate, dermatan sulfate, heparan sulfate, keratan sulfate, carrageenan, pectin, heparin, dextran, dextran sulfate, and sulfated glucan; thereby increasing the subjects bone density.

14. A method for lowering the serum calcium level in a subject in need thereof, comprising administering to said subject a composition comprising an amount of human osteoclastogenesis inhibitory factor (OCIF) protein and a polysaccharide, effective in combination for lowering the serum calcium level, wherein said polysaccharide is selected from the group consisting of: hyaluronic acid, chondroitin sulfate, dermatan sulfate, heparan sulfate, keratan sulfate, carrageenan, pectin, heparin, dextran, dextran sulfate, and sulfated glucan, thereby lowering the serum calcium level in said subject.

15. The method of claim 14, wherein said polysaccharide is selected from the group consisting of: heparin, pectin, carrageenan, and dextran sulfate.

16. The method of claim 14, wherein said polysaccharide is selected from the group consisting of: heparin having a molecular weight of 3,000 to 6,000, and dextran sulfate having a molecular weight of 5,000 to 10,000.

17. The method of claim 14, wherein the weight ratio of human OCIF protein to polysaccharide is at least about 1:4.

18. The method of claim 14, wherein said composition is a liquid composition.

19. The method of claim 14, wherein said composition is a lyophilized composition.

20. A method for lowering the serum calcium level in a subject in need thereof, comprising administering to said subject a composition comprising an amount of human osteoclastogenesis inhibitory factor (OCIF) protein homolog and a polysaccharide, effective in combination for lowering the serum calcium level in said subject, wherein said OCIF protein homolog is selected from the group consisting of human OCIF2, human OCIF3, human OCIF4, and human OCIF5, and said polysaccharide is selected from the group consisting of: hyaluronic acid, chondroitin sulfate, dermatan sulfate, heparan sulfate, keratan sulfate, carrageenan, pectin, heparin, dextran, dextran sulfate, and sulfated glucan, thereby lowering the subjects serum calcium level.

21. A method for prolonging the persistence of human osteoclastogenesis inhibitory factor (OCIF) protein in a subject in need of treatment with OCIF, said method comprising administering an effective amount of said human OCIF protein to said subject in conjunction with an amount of a polysaccharide effective for prolonging the persistence of OCIF in the serum of said subject, wherein said polysaccharide is selected from the group consisting of: hyaluronic acid, chondroitin sulfate, dermatan sulfate, heparan sulfate, keratan sulfate, carrageenan, pectin, heparin, dextran, dextran sulfate, and sulfated glucan;

wherein the persistence of said human OCIF protein, administered with said polysaccharide, in said subjects serum is prolonged relative to the persistence of said human OCIF protein when administered in the absence of said polysaccharide.

22. The method of claim 21, wherein said polysaccharide is selected from the group consisting of: heparin, pectin, carrageenan, and dextran sulfate.

23. The method of claim 21, wherein said polysaccharide is selected from the group consisting of: heparin having a molecular weight of 3,000 to 6,000, and dextran sulfate having a molecular weight of 5,000 to 10,000.

24. The method of claim 21, wherein the weight ratio of human OCIF protein to polysaccharide is at least about 1:4.

25. The method of claim 21, wherein said composition is a liquid composition.

26. The method of claim 21, wherein said composition is a lyophilized composition.

27. A method for prolonging the persistence of a human osteoclastogenesis inhibitory factor (OCIF) protein homolog selected from the group consisting of human OCIF2, human OCIF3, human OCIF4, and human OCIF5, in a subject in need of treatment with said OCIF homolog, said method comprising administering an effective amount of said human OCIF protein homolog to said subject in conjunction with an amount of a polysaccharide effective for prolonging the persistence of said OCIF homolog in the serum of said subject, wherein said polysaccharide is selected from the group consisting of: hyaluronic acid, chondroitin sulfate, dermatan sulfate, heparan sulfate, keratan sulfate, carrageenan, pectin, heparin, dextran, dextran sulfate, and sulfated glucan;

wherein the persistence of said human OCIF protein homolog, administered with said polysaccharide, in said subjects serum is prolonged relative to the persistence of said human OCIF protein homolog when administered in the absence of said polysaccharide.

28. A medicinal composition for treating a bone-pathobolism selected from the group consisting of: osteoporosis, hypercalcemia and chronic articular rheumatism, said composition comprising: a human osteoclastogenesis inhibitory factor (OCIF) protein homolog selected from the group consisting of human OCIF2, human OCIF3, human OCIF4, and human OCIF5; and a polysaccharide selected from the group consisting of: hyaluronic acid, chondroitin sulfate, dermatan sulfate, heparan sulfate, keratan sulfate, carrageenan, pectin, heparin, dextran, dextran sulfate, and sulfated glucan.

29. A lyophilized medicinal composition for treating a bone-pathobolism selected from the group consisting of: osteoporosis, hypercalcemia and chronic articular rheumatism, said composition comprising: a human osteoclastogenesis inhibitory factor (OCIF) protein homolog selected from the group consisting of human OCIF2, human OCIF3, human OCIF4, and human OCIF5, and a polysaccharide selected from the group consisting of: hyaluronic acid, chondroitin sulfate, dermatan sulfate, heparan sulfate, keratan sulfate, carrageenan, pectin, heparin, dextran, dextran sulfate, and sulfated glucan.

30. A method of preparing a lyophilized medicinal composition for treating a bone-pathobolism selected from the group consisting of osteoporosis, hypercalcemia and chronic articular rheumatism, said composition comprising a human osteoclastogenesis inhibitory factor (OCIF) protein homolog selected from the group consisting of human OCIF2, human OCIF3, human OCIF4, and human OCIF5, and a polysaccharide selected from the group consisting of: hyaluronic acid, chondroitin sulfate, dermatan sulfate, heparan sulfate, keratan sulfate, carrageenan, pectin, heparin, dextran, dextran sulfate, and sulfated glucan, said method comprising:

dissolving OCIF homolog and said polysaccharide in a solution; and freeze-drying the solution comprising said OCIF homolog and said polysaccharide.

* * * * *